(12) United States Patent
Dekel et al.

(10) Patent No.: US 12,029,502 B2
(45) Date of Patent: Jul. 9, 2024

(54) SURGICAL TOOL CALIBRATION

(71) Applicant: Claronav Inc., North York (CA)

(72) Inventors: Doron Dekel, Toronto (CA); Arish Qazi, Oakville (CA)

(73) Assignee: CLARONAV INC., North York (CA)

(*) Notice: Subject to any disclaimer, the term of this patent is extended or adjusted under 35 U.S.C. 154(b) by 386 days.

(21) Appl. No.: 17/540,293

(22) Filed: Dec. 2, 2021

(65) Prior Publication Data

US 2022/0175463 A1 Jun. 9, 2022

Related U.S. Application Data

(60) Provisional application No. 63/121,413, filed on Dec. 4, 2020.

(51) Int. Cl.
| | |
|---|---|
| *A61B 5/00* | (2006.01) |
| *A61B 34/20* | (2016.01) |
| *G06T 7/00* | (2017.01) |
| *G06T 7/30* | (2017.01) |
| *G06T 7/70* | (2017.01) |
| *G06V 10/20* | (2022.01) |
| *G06V 10/22* | (2022.01) |
| *G06V 20/50* | (2022.01) |
| *H04N 23/90* | (2023.01) |

(52) U.S. Cl.
CPC ............ *A61B 34/20* (2016.02); *G06T 7/0014* (2013.01); *G06T 7/30* (2017.01); *G06T 7/70* (2017.01); *G06V 10/22* (2022.01); *G06V 10/255* (2022.01); *G06V 20/50* (2022.01); *H04N 23/90* (2023.01); *G06T 2200/04* (2013.01); *G06T 2207/30004* (2013.01); *G06V 2201/034* (2022.01)

(58) Field of Classification Search
CPC .. A61B 34/20; G06T 7/30; G06T 7/70; G06T 7/0014; G06T 2207/30004
See application file for complete search history.

(56) References Cited

U.S. PATENT DOCUMENTS

| | | | |
|---|---|---|---|
| 7,043,961 | B2 | 5/2006 | Pandey et al. |
| 7,166,114 | B2 | 1/2007 | Moctezuma De La Barrera et al. |
| 10,449,005 | B2 | 10/2019 | Christian et al. |
| 2003/0040879 | A1 | 2/2003 | Jutras et al. |

(Continued)

FOREIGN PATENT DOCUMENTS

| | | |
|---|---|---|
| CN | 112022350 A | 12/2020 |
| WO | 2019227215 A1 | 12/2019 |

*Primary Examiner* — Joel F Brutus
(74) *Attorney, Agent, or Firm* — Bereskin & Parr LLP/S.E.N.C.R.L., s.r.l.

(57) ABSTRACT

A system and method of operating a surgical navigation system to determine the location of a point of interest (POI) in a 3D coordinate frame of a surgical tool (tool frame) using a calibrated imaging device to capture an image of a portion of the surgical tool's surface the calibrated imaging device having calibration data that enables a processor of the surgical navigation system to map from a 2D location in the image to a projection line in a 3D coordinate frame of the imaging device (image frame). The system is operated to determine a mapping between an image frame and a tool frame. The processor is operated to determine the location of the POI in the tool frame based on the image and the mapping between the image frame and the tool frame.

20 Claims, 4 Drawing Sheets

(56) References Cited

U.S. PATENT DOCUMENTS

| | | | |
|---|---|---|---|
| 2004/0015176 A1* | 1/2004 | Cosman | A61B 90/14 |
| | | | 606/131 |
| 2004/0039402 A1 | 2/2004 | Zeiss et al. | |
| 2009/0163930 A1 | 6/2009 | Aoude et al. | |
| 2018/0263725 A1* | 9/2018 | Pesach | A61C 9/0053 |
| 2019/0329407 A1* | 10/2019 | Qi | G05D 1/0248 |

* cited by examiner

SURGICAL TOOL CALIBRATION

PRIORITY

This application claims the benefit of U.S. Provisional Patent Application No. 63/121,413, filed Dec. 4, 2020, which is incorporated herein by reference in its entirety.

FIELD

The described embodiments relate to the field of medical devices, in particular, the field of surgical navigation systems.

INTRODUCTION

In a typical surgical navigation system, a stereoscopic pose tracking sub-system dynamically tracks the pose of an optical marker rigidly attached to the tool being navigated. The position of the tip of the tool being tracked in the 3D coordinate frame of the optical marker is obtained using a measurement process called "tooltip calibration". In typical calibration systems, the calibration of the tooltip is accomplished by requiring the user to press the tooltip against a surface feature, such as a bore hole, a groove, or a dimple, of a calibration device simultaneously tracked by the pose tracking sub-system. That surface feature has a position and shape known to the navigation system (e.g., U.S. Pat. No. 7,166,114, U.S. 2003/0040879), which is then used to compute the tip's position. Alternatively, the user is instructed to move the tool around a tooltip location fixed by a surface feature, and the system computes the tooltip position by estimating that fixed location from measuring the movements. These calibration methods interrupt the surgical workflow, may introduce inaccuracies due to user errors and require additional preparation steps such as sterilization of the calibration device.

Furthermore, the calibration device is designed to work for specific tip shapes and specific points of interest (POIs) on, or in, the tip, and thus the range of accurately calibratable tooltips is limited.

SUMMARY

The various embodiments described herein generally relate to systems and methods for locating a point of interest (POI) on, inside or near, a surgical tool for the purpose of providing navigational guidance to manipulate that tool during surgery. An example surgical navigation system for locating a point of interest on a surgical tool includes:
  a processor;
  a surgical tool having a point of interest (POI) in a 3D coordinate frame of the surgical tool (tool frame);
  a calibrated imaging device configured to capture an image of a portion of the surgical tool's surface, the calibrated imaging device having calibration data that enables the processor of the surgical navigation system to map from a 2D location in the image to a light projection line in a 3D coordinate frame of the imaging device (image frame),
  wherein the processor is configured to:
  determine a mapping between the image frame and the tool frame; and
  determine the location of the POI in the tool frame based on the image and the mapping between the tool frame and the image frame.

In any embodiment, to determine the location of the POI in the tool frame, the processor can be further configured to:
  recognize a POI projection location on the image based on the appearance of the portion of the tool's surface in the image;
  compute 2D coordinates for the POI projection location on the image;
  compute a POI projection line in the image frame corresponding to the POI projection location based on the calibration data; and
  determine the location of the POI in the tool frame based on at least the POI projection line and the mapping between the image frame and the tool frame.

In any embodiment, the processor can be further configured to determine the location of the POI in the tool frame based additionally on selecting a location on the POI projection line based on intersecting the projection line with at least one line or surface in the tool frame on which the POI is known to lie.

In any embodiment, the at least one line or surface can comprise a tooltip axis of rotation and the processor can be further configured to select the location on the POI projection line by computing an intersection location between the POI projection line and the tooltip axis of rotation.

In any embodiment, the surface of the surgical tool can comprise a patient-contacting portion and the processor can be further configured to obtain shape parameters of the patient-contacting portion.

In any embodiment, determining the location of the POI in the tool frame can comprise:
  a second calibrated imaging device configured to capture a second image of the portion of the surgical tool's surface from a different viewing angle than the first image, the second calibrated imaging device having second calibration data that enables the processor to map from a 2D location in the second image to a projection line in a second image frame, the second image frame being a 3D coordinate frame of the second imaging device,
  wherein the processor can be further configured to:
  determine a mapping between the second image frame and the tool frame;
  recognize a second POI projection location on the second image based on the appearance of the portion of the tool's surface in the second image, compute 2D coordinates for a second POI projection location on the second image;
  based on the second calibration data, compute a second POI projection line in the second image frame corresponding to the second POI projection location, and
  determine the location of the POI in the tool frame by computing an intersection location between the POI projection line and the second POI projection line.

In any embodiment, the processor can be configured to determine the mapping between the image frame and the tool frame based on the image of the portion of the surgical tool's surface.

In any embodiment, the calibrated imaging device can be further configured to capture a plurality of images of the portion of the surgical tool's surface, each image in the plurality of images being taken from a different viewing angle, and the processor can be further configured, for each image in the plurality of images, to:
  recognize the POI projection location on that image based on the appearance of the portion of the tool's surface in that image in the plurality of images;

compute 2D coordinates for the POI projection location on that image;

based on the calibration data, compute a POI projection line in the image frame corresponding to the POI projection location on that image, and determine the location of the POI in the tool frame by computing an intersection location between each of the POI projection lines.

In any embodiment, the calibrated imaging device can be configured to capture a plurality of images of the portion of the surgical tool's surface, each image in the plurality of images having a different mapping between that image's frame and the tool frame, and the processor can be further configured to:

compute a tool surface projection contour search region in each image in the plurality of images based on the mapping of each image, each tool surface projection contour search region having a plurality of pixel values;

align the tool surface projection contour search region in the plurality of images; and compute the POI projection location based on combining the pixel values in the aligned tool surface projection contour search regions such that pixel locations corresponding to aligned edges are distinguishable from pixel values corresponding to non-aligned edges.

In any embodiment, the processor can be further configured to:

select a first location and a second location in the tool frame based on a spatial region defined by the surgical tool;

map the first location and the second location from the tool frame to the image;

resample the image in a rectangular grid to form a resampled image, the rectangular grid having rows and columns wherein the first and second location lie on the same row or column;

use image processing to locate 2D coordinates for a resampled POI projection location in the image frame;

map the 2D coordinates of the resampled POI projection location to the image; and compute the 2D coordinates for the POI projection location on the image.

In any embodiment, the processor can be further configured to:

store the location of the POI in a computer-readable memory, and during a plurality of times in a time interval, at each time in the plurality of times in the time interval, the processor is configured to:

operate the surgical navigation system to determine a mapping between the image frame and the tool frame; and operate the processor to determine whether to update the stored POI location based on the mapping between the image frame and the tool frame.

An example method of operating a surgical navigation system to determine the location of a point of interest (POI) in a 3D coordinate frame of a surgical tool (tool frame) involves:

using a calibrated imaging device to capture an image of a portion of the surgical tool's surface, the calibrated imaging device having calibration data that enables a processor of the surgical navigation system to map from a 2D location in the image to a light projection line in a 3D coordinate frame of the imaging device (image frame);

operating the surgical navigation system to determine a mapping between the image frame and the tool frame; and operating the processor of the surgical navigation system to determine the location of the POI in the tool frame based on the image and the mapping between the image frame and the tool frame.

In any embodiment, operating the processor of the surgical navigation system to determine the location of the POI can comprise operating the processor to:

recognize the POI projection location on the image based on the appearance of the portion of the tool's surface in the image;

compute 2D coordinates for the POI projection location on the image;

compute a POI projection line in the image frame corresponding to the POI projection location based on the calibration data; and determine the location of the POI in the tool frame based on at least the POI projection line and the mapping between the image frame and the tool frame.

In any embodiment, operating the processor to determine the location of the POI in the tool frame can be additionally based on selecting a location on the POI projection line based on intersecting the projection line with at least one line or surface in the tool frame on which the POI is known to lie.

In any embodiment, the at least one line or surface can comprise a tooltip axis of rotation and selecting the location on the POI projection line can comprise computing an intersection location between the POI projection line and the tooltip axis of rotation.

In any embodiment, the surface of the surgical tool can comprise a patient-contacting portion and the method can further comprise operating the processor to obtain shape parameters of the patient-contacting portion.

In any embodiment, determining the location of the POI in the tool frame can comprise:

using a second calibrated imaging device to capture a second image of the portion of the surgical tool's surface from a different viewing angle than the first image, the second calibrated imaging device having second calibration data that enables the processor to map from a 2D location in the second image to a second image frame, the second image frame being a 3D coordinate frame of the second imaging device;

operating the surgical navigation system to determine a mapping between the second image frame and the tool frame;

operating the processor of the surgical navigation system to:

recognize a second POI projection location on the second image based on the appearance of the portion of the tool's surface in the second image;

compute 2D coordinates for a second POI projection location on the second image;

based on the second calibration data, compute a second POI projection line in the second image frame corresponding to the second POI projection location, wherein operating the processor to determine the location of the POI in the tool frame can further comprise computing an intersection location between the POI projection line and the second POI projection line.

In any embodiment, determining the mapping between the image frame and the tool frame can be based on the image of the portion of the surgical tool's surface.

In any embodiment, the method can further comprise using the calibrated imaging device to capture a plurality of images of the portion of the surgical tool's surface, each image in the plurality of images being taken from a different viewing angle; and operating the processor of the surgical navigation system to, for each image in the plurality of images:
recognize the POI projection location on that image based on the appearance of the portion of the tool's surface in that image;
compute 2D coordinates for the POI projection location on that image;
based on the calibration data, compute a POI projection line in the image frame corresponding to the POI projection location on that image; and
wherein operating the processor to determine the location of the POI in the tool frame can further comprise computing an intersection location between each of the POI projection lines.

In any embodiment, the method can further comprise using the calibrated imaging device to capture a plurality of images of the portion of the surgical tool's surface, each image in the plurality of images having a different mapping between that image's frame and the tool frame, and wherein operating the processor to compute 2D coordinates for the POI projection location in the image can further comprise operating the processor to:
compute a tool surface projection contour search region in each image in the plurality of images based the mapping of each image, each tool surface projection contour search region having a plurality of pixel values;
align the tool surface projection contour search regions in the plurality of images; and
compute the POI projection location based on combining the pixel values in the aligned tool surface projection contour search regions such that pixel locations corresponding to aligned edges are distinguishable from pixel values corresponding to non-aligned edges.

In any embodiment, computing the 2D coordinates for the POI projection location on the image can further comprise operating the processor to:
select a first location and a second location in the tool frame based on a spatial region defined by the surgical tool;
map the first location and the second location from the tool frame to the image;
resample the image in a rectangular grid to form a resampled image, the rectangular grid having rows and columns wherein the first and second location lie on the same row or column;
use image processing to locate 2D coordinates for a resampled POI projection location in the image frame;
map the 2D coordinates of the resampled POI projection location to the image.

In any embodiment, the method can further comprise storing the location of the POI in a computer-readable memory and during a plurality of times in a time interval, at each time in the plurality of times in the time interval:
operating the surgical navigation system to determine a mapping between the image frame and the tool frame; and
operating the processor to determine whether to update the stored POI location based on the mapping between the image frame and the tool frame.

These and other aspects and features of various embodiments will be described in greater detail below.

BRIEF DESCRIPTION OF THE DRAWINGS

Several embodiments will now be described in detail with reference to the drawings, in which.

Figure 1:
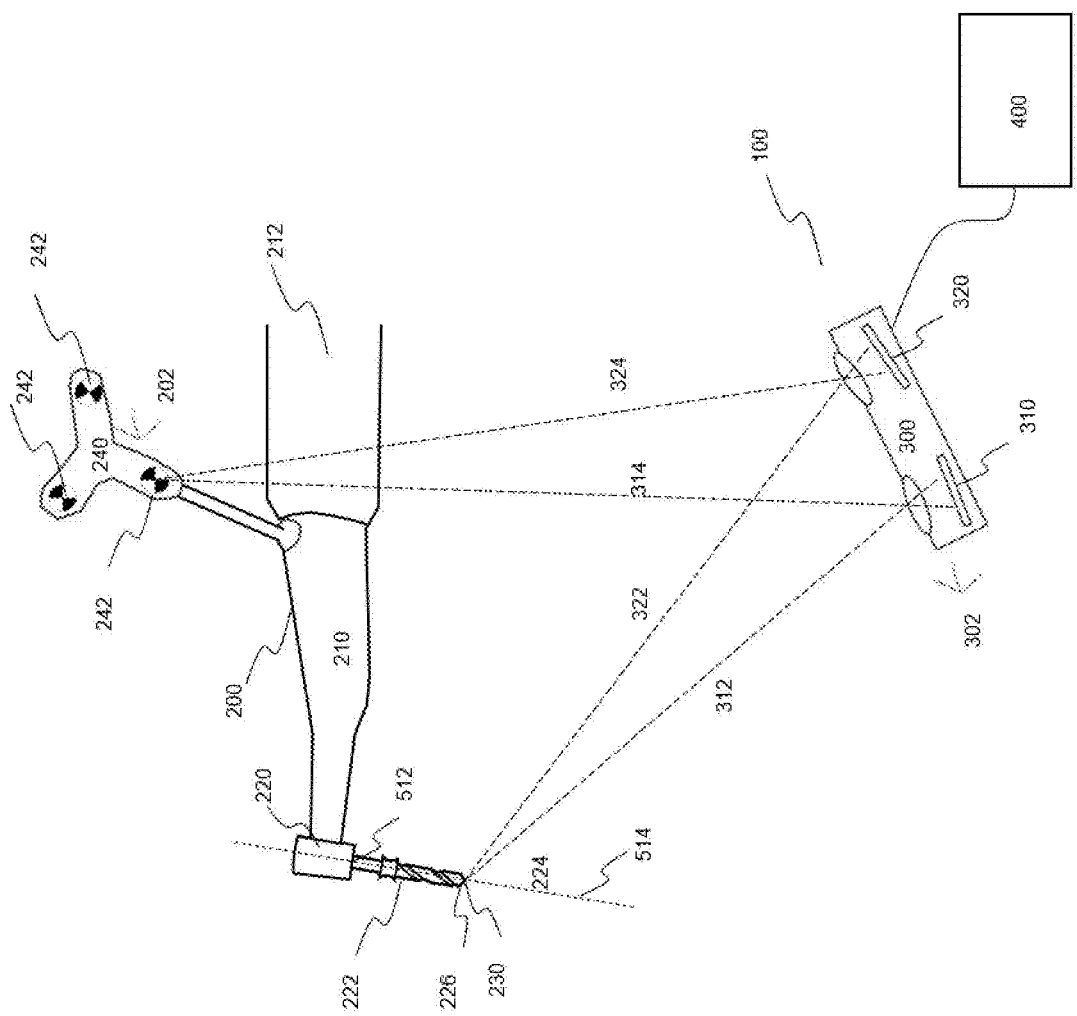
FIG. 1 is an example illustration of a surgical navigation system for locating a point of interest on a surgical tool, according to at least one embodiment.

The drawings, described below, are provided for purposes of illustration, and not of limitation, of the aspects and features of various examples of embodiments described herein. For simplicity and clarity of illustration, elements shown in the drawings have not necessarily been drawn to scale. The dimensions of some of the elements may be exaggerated relative to other elements for clarity. It will be appreciated that for simplicity and clarity of illustration, where considered appropriate, reference numerals may be repeated among the drawings to indicate corresponding or analogous elements or steps.

DESCRIPTION OF EXAMPLE EMBODIMENTS

It will be appreciated that numerous specific details are set forth in order to provide a thorough understanding of the example embodiments described herein. However, it will be understood by those of ordinary skill in the art that the embodiments described herein may be practiced without these specific details. In other instances, well-known methods, procedures and components have not been described in detail so as not to obscure the embodiments described herein. Furthermore, this description and the drawings are not to be considered as limiting the scope of the embodiments described herein in any way, but rather as merely describing the implementation of the various embodiments described herein.

It should be noted that terms of degree such as "substantially", "about" and "approximately" when used herein mean a reasonable amount of deviation of the modified term such that the end result is not significantly changed. These terms of degree should be construed as including a deviation of the modified term if this deviation would not negate the meaning of the term it modifies.

In addition, as used herein, the wording "and/or" is intended to represent an inclusive-or. That is, "X and/or Y" is intended to mean X or Y or both, for example. As a further example, "X, Y, and/or Z" is intended to mean X or Y or Z or any combination thereof.

It should be noted that the term "coupled" used herein indicates that two elements can be directly coupled to one another or coupled to one another through one or more intermediate elements.

In at least one embodiment, aspects of methods described herein, such as method 1000 described with reference to FIG. 4 below, may be implemented in hardware or software, or a combination of both. These embodiments may be implemented in computer programs executing on programmable computers, each computer including at least one processor, a data storage system (including volatile memory or non-volatile memory or other data storage elements or a combination thereof), and at least one communication component. For example, and without limitation, the programmable computer (referred to below as data processor) may be a server, network appliance, embedded device, computer expansion module, a personal computer, laptop, personal data assistant, cellular telephone, smart-phone device, tablet computer, a wireless device or any other computing device capable of being configured to carry out the methods described herein.

In at least one embodiment, the communication component may be a network communication interface. In embodiments in which elements are combined, the communication component may be a software communication interface, such as those for inter-process communication (IPC). In still other embodiments, there may be a combination of communication components implemented as hardware, software, and combination thereof.

Program code may be applied to input data to perform the functions described herein and to generate output information. The output information is applied to one or more output devices, in known fashion.

Each program may be implemented in a high level procedural or object oriented programming and/or scripting language, or both, to communicate with a computer system. However, the programs may be implemented in assembly or machine language, if desired. In any case, the language may be a compiled or interpreted language. Each such computer program may be stored on a storage media or a device (e.g., ROM, magnetic disk, optical disc) readable by a general or special purpose programmable computer, for configuring and operating the computer when the storage media or device is read by the computer to perform the procedures described herein. Embodiments of the system may also be considered to be implemented as a non-transitory computer-readable storage medium, configured with a computer program, where the storage medium so configured causes a computer to operate in a specific and predefined manner to perform the functions described herein.

Referring now to FIG. 1, shown therein is an example illustration of a system 100 for determining the location of a point of interest (POI) in a 3D coordinate frame of a surgical tool, according to at least one embodiment. The system 100 includes a surgical tool 200, a calibrated imaging device 300, and a processor 400. The use of the calibrated imaging device 300 can eliminate the need of a calibration device in surgical navigation systems by use of image processing.

The surgical tool 200 may be any tool used during any type of surgery. In the example shown, the surgical tool 200 is a dental handpiece. The surgical tool 200 has a body 210 with a motor 212 for driving a rotating chuck inside the handpiece's head. In at least one embodiment, the tool can be another type of power tool, such as a screwdriver or a vibrating saw, or a passive tool, such as a probe or a pointer with a conical, rounded, or spherical tip.

The surgical navigation system 100 can be used to perform calibration of one or more points of interest (POI) to the user on or inside the surgical tool 200, typically at, or in the vicinity of, a patient-contacting surface of the tool. The POI, or POIs, of the surgical tool 200 may vary depending on the desired use of the tool 200. For example, the surgical tool 200 may have an exchangeable rotating bit with a fixed axis of rotation 224 in the frame of the tool 200, which, since it is fixed relative to the optical tracker 240 for all rotating bits, may be calibrated separately in advance of any bit being inserted into the tool's chuck, such as by using a special trackable bit. The calibration in advance of the rotating axis of any bit being inserted into the chuck may be performed by any means. The result of the axis calibration can be stored in a persistent memory of the processor 400 for retrieval on demand.

Once a drill bit has been inserted in the chuck, the POI will typically be the location of a tip of the bit along the pre-calibrated rotation axis. In at least one embodiment, the tip of the tool 200 may be fixed to the tool 200 (i.e., not exchangeable), but the position of the tip in the tool's frame may have changed due to, for example, bending of the tip during or between uses due to an accidental hit. In at least one embodiment, the tool 200 may have a repositionable tip that is moveable relative to the frame of the tool 200 along a restricted curve or within a restricted region. For example, an exchangeable tip may be screwed on to the tool's body 200 using a helical thread such that its POI may vary along a substantially circular path depending on the orientation of the tip when the screwing process starts and the amount of tightening force.

In the example shown, the tool 200 has a chuck 220 for receiving an exchangeable bit part 222. The exchangeable bit part 222 may be any bit that is used during surgery. For example, in the example shown, the bit part 222 is a drill bit. The bit part 222 is inserted into the chuck 220, which may be used to rotate the bit part 222 about its bit axis 224. The bit 222 has a patient-contacting portion 226, which may also be referred to as a tooltip. In at least one embodiment, the bit 222 can be fixed or repositionable along a bit path and/or non-removable or removable.

The calibrated imaging device 300 may be any device capable of capturing an image of at least a portion of the surgical tool 200. For example, in the example shown in FIG. 1, the calibrated imaging device 300 is a stereoscopic camera having a first sensor 310 and a second sensor 320. The first sensor 310 and the second sensor 320 can capture simultaneous projections of light reflecting off of the surgical field (i.e., a spatial region where the POI is located), allowing for the capturing of images from two viewing angles. Associated with imaging device 300 is a coordinates frame 302, which is a 3D coordinate frame for specifying positions relative to the body of imaging device 300. The calibrated imaging device 300 includes calibration data that enables the use of light being measured at a 2D pixel location in sensor 310 and/or sensor 320 to map to a projection line in the image frame 302.

In other words, a POI projection location can be recognized by the processor on the image based on the appearance of the portion of the tool's surface in the image. Recognizing the POI projection location in the image can be based on implicit or explicit assumptions about the locations where the POI 230 lies in the tool frame 202. For example, the POI location can be recognized by, including, but not limited to, marking the POI location with a red dot against a blue background with the processor 400 being configured to recognize that colour pattern in the image, geometrical features of the projection of the surface of surgical tool 200 in the vicinity of the POI such as parallel edges of the projection of a cylindrical section, and/or a convolutional neural network that can be trained to enable the processor 400 to recognize the POI using example images showing a portion of the tool's surface and annotated with the POI location.

The recognition can be made more reliable by using multiple images of the tool from multiple different viewing angles, for example by using a stereoscopic camera providing two different viewing angles to help distinguish between tool and background pixels and reduce measurement noise, as shown in FIG. 1. In at least one embodiment, the calibrated imaging device 300 can be monoscopic and can have a single lens and a single image sensor. The reliability of distinguishing between tool and background pixels can also be improved by using a sequence of captured images where the tool is moving in relation to a fixed background, as will be further described below.

The surgical tool 200 has a 3D coordinate tool frame 202 that moves with the tool 200. The tool frame 202 may be determined by use of the calibrated imaging device 300, or by any other means. For example, in the example shown, the tool 200 has a trackable target 240 rigidly coupled to the tool 200, such that the trackable target 240 shares the tool frame 202. In the example shown, the trackable target 240 is an optical marker having three optical targets 242. The optical targets 242 may be tracked with the calibrated imaging device 300, another imaging device, or both, to track the tool frame 202.

The processor 400 is in data communication with an image data stream generated by the imaging device 300. The processor 400 may be a single component, or may be implemented as several connected computing elements. The processor 400 can process image data from the imaging device 300 and can use the stored calibration data to compute a mapping between the tool frame 202 and the image frame 302. The imaging device 300 may be used for pose tracking using stereoscopic and monoscopic motion tracking methods. In such a case, the image data stream of the calibrated imaging device 300 may be used to both map between the tool frame 202 and the image frame 302 and to calibrate the tool's POI as described herein.

The surgical navigation system 100 can be used to determine the 2D location of the POI 230 in the tool frame based on recognizing a spatial region of the tool 200 on, or near, which the POI is known to lie. The POI 230 may be on or within a surface of the tool 200, located on or inside the exchangeable tooltip 222 of the tool 200, and can be located along a curve. For example, in the example shown in FIG. 1, the POI 230 is the tooltip 226 of the bit 222 and the spatial region includes the bit axis 224, such that the bit axis 224 defines the straight line segment, which is a simple curve, on which the POI 230 must lie. In another example, in the example shown in FIG. 3, the POI (center 630) is located at the centre of a spherically shaped tip surface 222. In at least one embodiment, the bit 222 can be repositionable relative to the tool 200. For example, the one or more lockable joints can be used to reposition the bit 222.

In at least one embodiment, the range of possible locations where the tooltip 226 may be found can be defined by a path or surface that can be mathematically described in the tool frame 202. As described above, the possible locations may also be recognized by the processor 400 based on the appearance of the portion of the tool's surface in the image. For example, the POI may be at, or near, the tip of a bendable stem. The length, shape and material properties of the stem can limit the locations in which the POI lies to a curved surface in the tool frame 202, a descriptor of which can be obtained and stored in advance and used to limit the region in which the POI recognition is applied in 2D. This information can be subsequently used to localize the POI in 3D.

Figure 2:
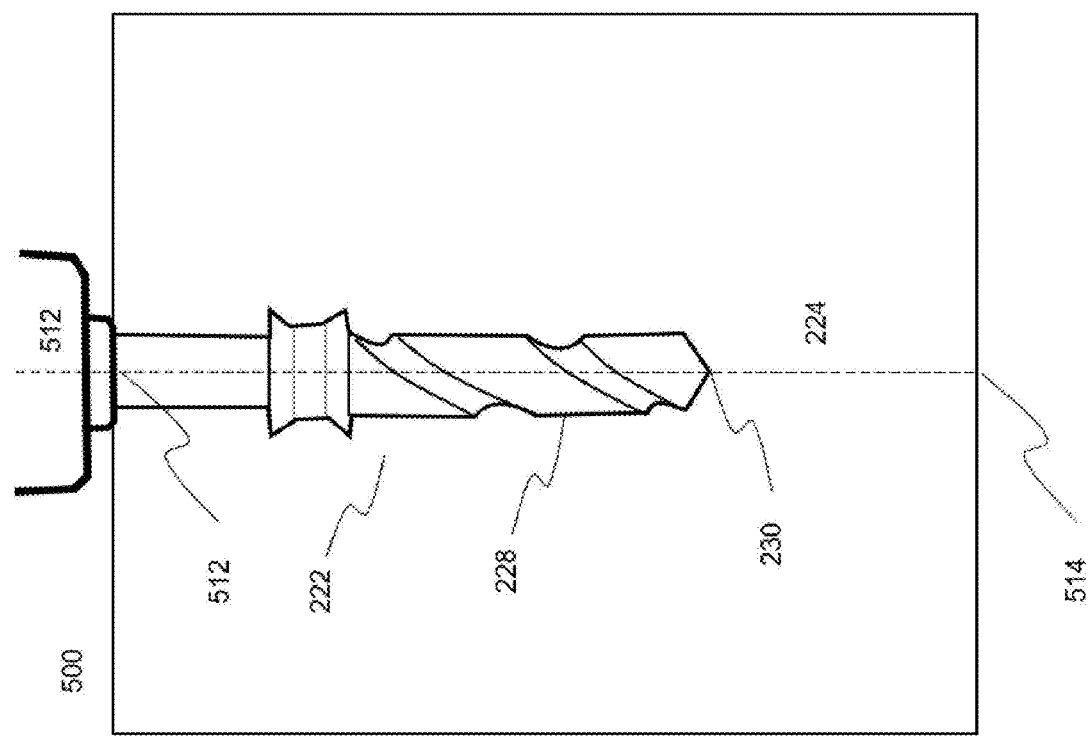
FIG. 2 is an example illustration of an image taken with the surgical navigation system of FIG. 1, according to at least one embodiment.

To locate the 2D coordinates of the POI 230 in the image, based on the appearance of the portion of the tool's surface in the image, a pixel location corresponding to the POI 230 can be computed. The determination of the pixel location corresponding to the POI 230 can vary with the type of bit used in the tool 200. For example, when the tool has a rotatable exchangeable bit, the bit axis 224 can be used to locate the pixel location corresponding to 2D coordinates of the POI 230 in the image taken by the imaging device 300. Referring to FIG. 2, a first location 512 and a second location 514 can be selected in the tool frame 202 based on the spatial region defined by the tool 200. In the example shown, the first location 512 is where the bit 222 exits the chuck 220 and the second location 514 is just beyond the longest possible bit whose tip needs to be detected. The first location 512 and the second location 514 can be mapped from the tool frame 202 to the image.

The image can be resampled in a rectangular grid to form a resampled POI search image 500. The rectangular grid has rows and columns where the first location 512 and the second location 514 lie on the same row or column. In the example shown in FIG. 2, the projection of the first location 512 is at the top middle of the resampled image 500 and the second location 514 is at the bottom middle of the region. The width of the region of the resampled image 500 can be determined based on the range of size appearances of the bits to be calibrated, which can be based on the width of the largest diameter bit to be used with the tool 200 and the closest distance this bit would be presented to the imaging device 300 during the calibration. For example, the width of the region can be several pixels wider than the appearance of the largest width of the bit to be used with the tool 200 at the shortest distance from the camera in which the bit would be in focus. The processor 400 can process the image to locate 2D coordinates for a resampled POI projection location in the image frame 302 and the 2D coordinates of the resampled POI projection location can be mapped to the image.

Image processing methods can be used to locate the coordinates of the POI 230 along the bit axis 224 column (or row) in the resampled image 500, or, alternatively, in the original image by mapping between coordinates aligned with the axis line 224 and image coordinates. In other words, the image may be resampled as needed without forming an explicit axis-aligned image. For example, the image processing method can include, but is not limited to, applying a convolutional neural network trained using a large number of bit images where the POI was manually marked, and/or edge detection methods relying on the approximate symmetry around the axis 224 of the appearance of bit's projection and the change in orientation of the edges near the POI 230.

Once the POI 230 is located in the resampled image 500, the 2D coordinates can be mapped back to the full image and provided to the processor 400 to compute one or more 3D projection lines between the image frame 302 and tool frame 202. Based on the calibration data of the imaging device 300, one or more 3D projection lines can be computed in the image frame 302 from the imaging device 300 to one or more locations on the tool 200. Referring to FIG. 1, in the example shown, the first sensor 310 projects a first projection line 312 to the POI 230 and a second projection line 314 to the tracker 240, while the second sensor 320 projects a third projection line 322 to the POI 230 and a fourth projection line 324 to the tracker 240.

The first projection line 312 and the third projection line 322 can be used by the surgical navigation system 100 to locate the 3D coordinates of the POI 230 in the tool frame 202. In the example shown in FIG. 1, the second projection line 314 and the fourth projection line 324, optionally with similar projection lines of other optical targets, can be used to locate the position of three or more optical targets 242 to compute the pose of tracker 240, thereby allowing the surgical navigation system 100 to map between the tool frame 202 and the image frame 302. Once the coordinate mapping between the tool frame 202 and the image frame 302 is computed, the projection lines of the imaging device 300 can be mapped to either of the two frames and intersected in the respective frame to determine the location of the POI 230.

In at least one embodiment, the tracking can be performed using different viewing angles projected from multiple imaging devices in different positions. For example, a separate calibrated imaging device can be used to determine the coordinate mapping between the image frame 302 and the tool frame 202 by tracking the imaging device 300 in its frame 302, while the imaging device 300 can be used to locate the POI 230 on the tool 200. In at least one embodiment, the tracking of the tool 200 can be performed by a non-optical method. For example, the tracking of the tool 200 can be performed using an electromagnetic tracking system.

The computation of the location of the POI 230 in the tool frame 202 can be based on the first projection line 312, the third projection line 322, and/or the spatial region in the tool frame 202 on which the POI 230 is known to lie. The spatial region where the POI lies in the tool frame 202 may include a line or surface in the tool frame 202 along which the POI 230 resides. For example, in the example shown in FIG. 1, the spatial region can include the bit axis 224, which contains the POI 230, since the axis 224 extends through the tooltip 226 and the POI 230 is located at the tooltip 226. The location of the POI in 3D can be computed using an intersection location between the projection line(s) and the tooltip axis 224. In the example shown in FIG. 1, the axis 224 can be intersected with one or both of the first projection line 312 and the third projection line 322 to locate the projection location.

In at least one embodiment, two intersecting lines can be used to locate the POI 230. For example, the first projection line 312 and the third projection line 322 can be used to intersect at the POI 230, without using the bit axis 224. In at least one embodiment, a single projection line, such as the first projection line 312, can be intersected with the bit axis 224 to locate the POI 230. In the example shown in FIG. 1, the first projection line 312 and third projection line 322 project along different viewing angles due to the positioning of the first sensor 310 and the second sensor 320.

In at least one embodiment, the calibrating imaging device 300 can be operated to capture a plurality of images of the portion of the surgical tool's surface, with each image being taken from a different viewing angle to enable the POI 230 to be computed by the interaction of multiple projection lines in the tool frame. The processor 400 can, for each image in the plurality of images, be operated to recognize the POI projection location on that image based on the appearance of the portion of the tool's surface in that image, compute 2D coordinates for the POI projection location on each image, and compute a POI projection line in the image frame 302 corresponding to the POI projection location on that image, and map that projection line to the tool frame 202. The location of the POI 230 in the tool frame 202 can then be computed by locating the intersection point between two or more projection lines from the plurality of images.

In at least one embodiment, the different views of the tool for the plurality of images can be obtained by moving the tool 200 to a different position and/or orientation such that the imaging device 300 captures a different viewing angle of the tool 200. For example, the tool 200 can be rotated and moved while the imaging device 300 captures multiple images from each of the different viewing directions. In at least one embodiment, the different viewing angles for the plurality of images can be obtained by the use of a plurality of imaging devices.

In at least one embodiment, the different viewing angles for the plurality of images can be obtained by using a second calibrated imaging device to capture a second image of the portion of the surgical tool's surface from a different viewing angle than the first image. The second calibrated imaging device can have second calibration data that enables the processor 400 to map from a 2D location in images taken by the second imaging device to a second image frame that is a 3D coordinate frame of the second imaging device.

In at least one embodiment, a plurality of images can be obtained where a projection of silhouette edges of bit 222 appear against a plurality of varying backgrounds. For example, such plurality of images can be obtained by stereo or different video frames in a sequence, or both. Using the mapping between tool and image frames, the regions in which the POI is searched can be aligned, for example by their boundaries and/or by a similarity-maximizing registration of their contents, and resampled into aligned search regions 500 such that edges 228 of the surface contour appear at similar locations in all the resampled regions. The plurality of aligned search regions can then be used to highlight or suppress pixels such that the bit 222 can be identified more clearly. For example, the POI projection location can be identified based on combining the pixel values in the aligned search regions such that pixel locations corresponding to aligned edges are more easily distinguishable from pixel locations corresponding to non-aligned edges. For example, pixel values in the same location can be averaged in the multiple aligned regions. Static edges in the aligned images can then remain detectable, while edges that move around (i.e., the background) can be blurred out by being averaged with non-edge pixels that map to the same location in other images. Other examples may include, but are not limited to, using median or summed pixel values, detecting edges in each of the images by first using edge detection algorithms to set binary pixels value (edge or non-edge) and then counting the edges that pass through, or in the near vicinity of, each pixel.

In at least one embodiment, one or more calibration limitations can be applied to the processor 400 to limit when the calibration occurs. These limitations can be added to the algorithm as quality control measures to improve its reliability and accuracy. For example, in at least one embodiment, the system 100 can include a computer-readable memory and the location of the POI 230 can be stored in the computer-readable memory. During a plurality of times in a time interval, at each time in the plurality of times in the time interval, the system 100 can be operated to determine a mapping between the image frame 302 and the tool frame 202. The processor 400 can be operated at each time in the plurality of times in the time interval to determine whether to update the stored POI location based on the mapping between the image frame 302 and the tool frame 202. In other words, the location of the POI at time t can be stored in the computer-readable memory. At a later time, the processor 400 can be operated to evaluate the mapping between tool frame 202 and image frame 302 to determine if the stored POI location should be recomputed and updated.

The processor 400 can determine whether to update the stored POI by using one or more conditions. For example, the processor 400 can compute a distance value corresponding to a distance between the imaging device 300 and the tool 200 and a viewing angle value between a line in the tool frame 202, such as the chuck's rotation axis 224, and a general viewing line between a location on the tool, such as 512, to the imaging device. Processor 400 then can compare the distance value to a distance value range and compare the viewing angle to an angle value range. When the distance value is within the distance value range and the viewing angle is within the angle value range, the processor 400 can be operated to determine the POI location and update the stored POI location. When the distance value is not within the distance value range or the viewing angle is not within the angle value range, the stored POI location is not updated. For example, if the tool 200 is too far or too close to the imaging device 300, the tool 200 may be out of focus. Accordingly, the system 100 can enable the calibration only when the tool 200 is within a certain range of viewing angles and distance, such that the tool 200 is more likely to be in focus, thereby improving the reliability of the calibration. In another example, to ensure that the POI location algorithm is applied only when the spatial region where the POI 230 lies in the tool frame is visible, the algorithm can be activated by the processor 400 only when the bit axis 224 is computed to be approximately perpendicular to the viewing line. That is, in this example, the calibration can occur only when the tooltip 226 is viewed from the side, as shown in FIG. 2.

In at least one embodiment, during the plurality of times in a time interval, at each time in the plurality of times in the time interval, the processor 400 can be operated to compute an orientation of the patient-contacting portion 226. When the orientation of the patient contacting portion 226 is substantially opposite to a direction of a gravitational force acting on the surgical tool 200, the processor 400 can be operated to determine the POI location and update the stored POI location, and when the orientation of the patient contacting portion 226 is not substantially opposite to the direction of the gravitational force acting on the surgical tool 200, the stored POI location is not updated. For example, the bit 222 can move slightly along the axis 224. When drilling, the force acting on the bit 222 causes the bit 222 to be pressed into the chuck 220. When not drilling and pointed downwardly, the bit 222 can move slightly out of the chuck 220. Accordingly, when the tooltip 226 is pointed upwardly, gravity can act on the bit 222 to pull it into the chuck 220 to a position similar to that of when the bit 222 is pressed against tissue, thereby providing for a more reliable calibration. These quality control measures can make the calibration more reliable and accurate.

Additional quality control measures can include, but are not limited to, evaluation of the strength and symmetry of the image edges considered in locating the tip in the image and/or using statistical analysis of the tip positions computed from multiple frames in the video stream to remove aberrant results and average out noise and jitter.

In at least one embodiment, the processor 400 can be operated to obtain shape parameters of the patient contacting portion 226. For example, a descriptor of an outer contour 228 of the bit 222 can be obtained. The outer contour 228 can be used to provide a geometrical description of a shape of the cutting volume of the bit 222 that will be removed when the bit 222 is rotated by the chuck 220. In other words, the descriptor of the outer contour can be used to provide additional information to the user during the surgery.

In at least one embodiment, the location of the POI for a fixed tooltip can be stored in the persistent memory of the processor 400 to allow the processor 400 to recalibrate as needed. For example, some tools, such as pointers or scalpels, have a fixed tip, typically at the end of a slender stem or blade that can be bent during surgery, such that the POI 230 changes between surgeries. The POI 230 can be recalibrated at the start of each surgery to compensate for the POI 230 moving between surgeries. The previous calibration can be used as an estimate of where the POI needs to be searched to verify the location of the POI has not changed, and if it did, to update that location. In other words, the POI location computed at one time can be used as the basis for an estimated position of the POI location for the computation that occurs at a later time.

Figure 3:
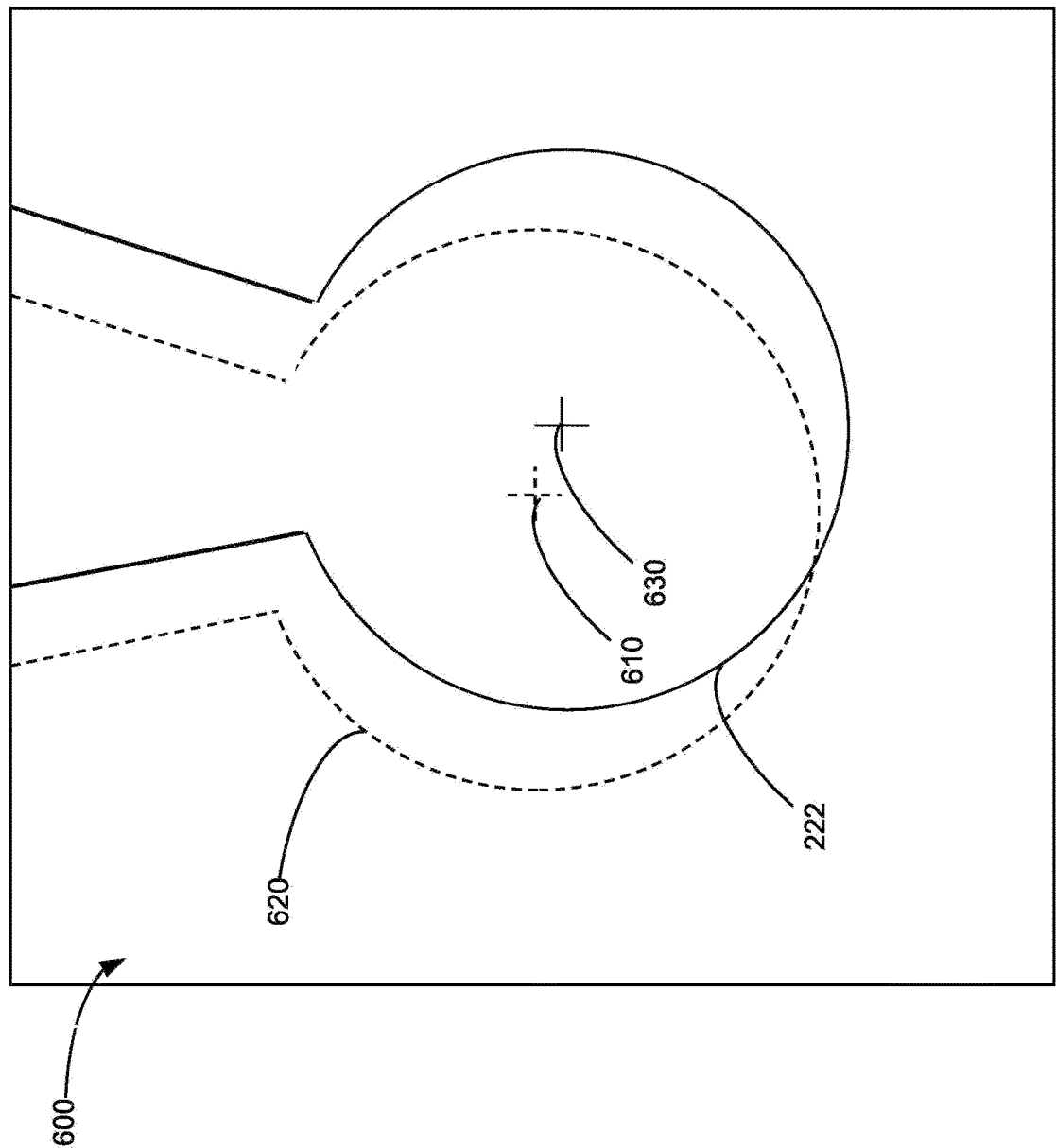
FIG. 3 is an example illustration of another image taken with the surgical navigation system of FIG. 1, according to at least one embodiment.

Referring to FIG. 3, the bit 222 has a substantially spherical tip having a known radius attached to a stem with the POI 630 being at the center of the sphere. During operation, the center of the sphere is projected on the image 600 at pixel 610 based on earlier measurement of the POI. The projected contour 620 of the spherical tip on the image 600 can be computed using the imaging device 300 and the image calibration data. The image 600 can be processed to determine the coordinates of the center of a circular edge nearby by searching in the vicinity of the projected center 610 to locate the actual projected center 630. The process can then be repeated from a different viewing angle, such as by using the two sensors of the imaging device 300 or by rotating the tooltip in front of the imaging device 300. Two or more sphere center projection lines can then be intersected to localize the sphere center (POI) in 3D.

Figure 4:
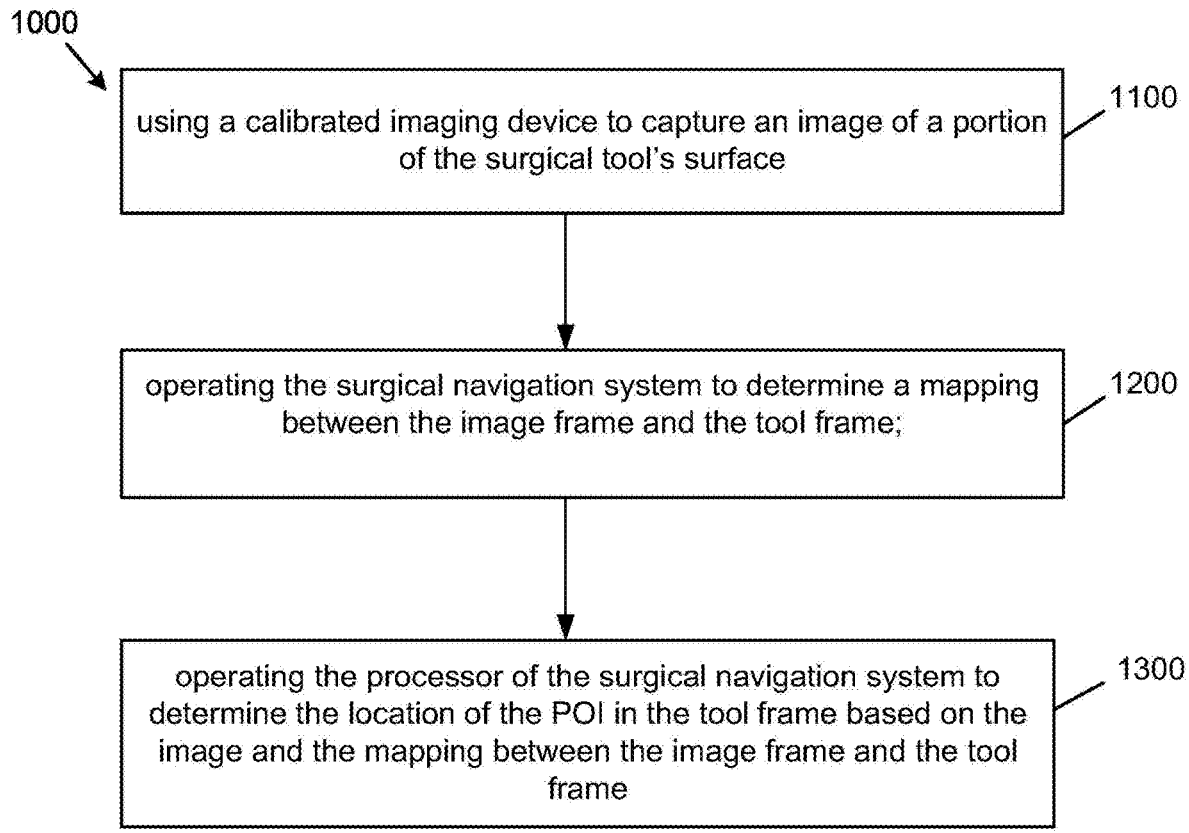
FIG. 4 is a flowchart of an example method of locating a point of interest on a surgical tool.

Referring to FIG. 4, shown therein is a flowchart of an example method 1000 of operating a surgical navigation system to determine the location of the POI in the tool frame 202.

At step 1100, the calibrated imaging device 300 is used to capture an image of a portion of the surgical tool's surface. As described previously, the calibrated imaging device has calibration data that enables the processor 400 of the surgical navigation system 100 to map from a 2D location in the image to a projection line in the 3D coordinate frame 302 of the imaging device.

At step 1200, the surgical navigation system 100 is operated to determine a mapping between the image frame 302 and the tool frame 202. The mapping may include any parameters that allow the processor 400 to compute locations between each coordinate frame. For example, the parameters may include position, distance, and/or viewing angle.

At step 1300, the processor 400 of the surgical navigation system 100 is operated to determine the location of the POI in the tool frame based on the image and the mapping between the image frame and the tool frame.

Optionally, the processor can be operated to: (i) recognize a POI projection location on the image based on the appearance of the portion of the tool's surface in the image; (ii) compute 2D coordinates for the POI projection location on the image; (iii) compute a POI projection line in the image frame corresponding to the POI projection location based on the calibration data; and (iv) determine the location of the POI 230 in the tool frame 202 based on at least the POI projection line and the mapping between the image frame 302 and the tool frame 202.

Optionally, the surgical navigation system 100 can be operated to determine the location of the POI in the tool frame 202 based on selecting a location on the POI projection line based on intersecting the projection line with at least one line or surface in the tool frame 202 on which the POI 230 is known to lie. In at least one embodiment, the POI 230 may not be visible on the surface of the tool 200. For example, in the example shown in FIG. 3, the POI 230 is shown at the center of the sphere at 630, which would not be visible in an image taken by the imaging device 300.

Various embodiments have been described herein by way of example only. Various modification and variations may be made to these example embodiments without departing from the spirit and scope of the invention, which is limited only by the appended claims.

The invention claimed is:

1. A method of operating a surgical navigation system to determine the location of a point of interest (a POI) in a 3D coordinate frame of a surgical tool (tool frame), the method comprising:
   a) using a calibrated imaging device to capture an image of a portion of a surface of the surgical tool, the calibrated imaging device having calibration data that enables a processor of the surgical navigation system to map from a 2D location in the image to a light projection line in a 3D coordinate frame of the calibrated imaging device (image frame);
   b) operating the surgical navigation system to determine a mapping between the image frame and the tool frame;
   c) operating the processor of the surgical navigation system to determine the location of the POI in the tool frame based on the image and the mapping between the image frame and the tool frame, wherein operating the processor of the surgical navigation system to determine the location of the POI comprises operating the processor to:
      i) recognize a POI projection location on the image based on the appearance of the portion of the surface of the tool in the image;
      ii) compute 2D coordinates for the POI projection location on the image;
      iii) compute a POI projection line in the image frame corresponding to the POI projection location based on the calibration data; and
      iv) determine the location of the POI in the tool frame based on at least the POI projection line and the mapping between the image frame and the tool frame.

2. The method of claim 1, wherein operating the processor to determine the location of the POI in the tool frame is additionally based on selecting a location on the POI projection line based on intersecting the projection line with at least one line or surface in the tool frame on which the POI is known to lie.

3. The method of claim 2, wherein the at least one line or surface comprises a tooltip axis of rotation and selecting the location on the POI projection line comprises computing an intersection location between the POI projection line and the tooltip axis of rotation.

4. The method of claim 1, wherein determining the location of the POI in the tool frame comprises:
   using a second calibrated imaging device to capture a second image of the portion of the surface of the surgical tool from a different viewing angle than the first image, the second calibrated imaging device having second calibration data that enables the processor to map from a 2D location in the second image to a projection line in a second image frame, the second image frame being a 3D coordinate frame of the second calibrated imaging device;
   operating the surgical navigation system to determine a mapping between the second image frame and the tool frame;
   operating the processor of the surgical navigation system to:
      i) recognize a second POI projection location on the second image based on the appearance of the portion of the surface of the tool in the second image;
      ii) compute 2D coordinates for a second POI projection location on the second image;
      iii) based on the second calibration data, compute a second POI projection line in the second image frame corresponding to the second POI projection location,
   wherein operating the processor to determine the location of the POI in the tool frame further comprises computing an intersection location between the POI projection line and the second POI projection line.

5. The method of claim 1, further comprising using the calibrated imaging device to capture a plurality of images of the portion of the surface of the surgical tool, each image in the plurality of images being taken from a different viewing angle; and
   operating the processor of the surgical navigation system to, for each image in the plurality of images:
      i) recognize the POI projection location on that image based on the appearance of the portion of the surface of the tool in that image;
      ii) compute 2D coordinates for the POI projection location on that image;
      iii) based on the calibration data, compute a POI projection line in the image frame corresponding to the POI projection location on that image; and
   wherein operating the processor to determine the location of the POI in the tool frame further comprises computing an intersection location between each of the POI projection lines.

6. The method of claim 1, further comprising using the calibrated imaging device to capture a plurality of images of the portion of the surface of the surgical tool, each image in the plurality of images having a different mapping between that image's frame and the tool frame, and wherein operating the processor to compute 2D coordinates for the POI projection location in the image further comprises operating the processor to:
   compute a tool surface projection contour search region in each image in the plurality of images based on the mapping of each image, each tool surface projection contour search region having a plurality of pixel values;
   align the tool surface projection contour search regions in the plurality of images; and
   compute the POI projection location based on combining the pixel values in the aligned tool surface projection contour search regions such that pixel locations corresponding to aligned edges are distinguishable from pixel values corresponding to non-aligned edges.

7. The method of claim 1, wherein computing the 2D coordinates for the POI projection location on the image further comprises operating the processor to:
   select a first location and a second location in the tool frame based on a spatial region defined by the surgical tool;
   map the first location and the second location from the tool frame to the image;
   resample the image in a rectangular grid to form a resampled image, the rectangular grid having rows and columns wherein the first location and the second location lie on the same row or column;
   use image processing to locate 2D coordinates for a resampled POI projection location in the image frame;

map the 2D coordinates of the resampled POI projection location to the image.

8. The method of claim 1, further comprising storing the location of the POI in a computer-readable memory and during a plurality of times in a time interval, at each time in the plurality of times in the time interval:
operating the surgical navigation system to determine a mapping between the image frame and the tool frame; and
operating the processor to determine whether to update the stored POI location based on the mapping between the image frame and the tool frame.

9. The method of claim 1, wherein the surface of the surgical tool comprises a patient-contacting portion and the method further comprises operating the processor to obtain shape parameters of the patient-contacting portion.

10. The method of claim 1, wherein determining the mapping between the image frame and the tool frame is based on the image of the portion of the surface of the surgical tool.

11. A surgical navigation system comprising:
a processor;
a surgical tool having a point of interest (a POI) in a 3D coordinate frame of the surgical tool (tool frame);
a calibrated imaging device configured to capture an image of a portion of a surface of the surgical tool, the calibrated imaging device having calibration data that enables the processor of the surgical navigation system to map from a 2D location in the image to a light projection line in a 3D coordinate frame of the calibrated imaging device (image frame),
wherein the processor is configured to:
i) determine a mapping between the image frame and the tool frame; and
ii) determine the location of the POI in the tool frame based on the image and the mapping between the image frame and the tool frame, wherein to determine the location of the POI in the tool frame, the processor is further configured to:
i) recognize a POI projection location on the image based on the appearance of the portion of the surface of the tool in the image;
ii) compute 2D coordinates for the POI projection location on the image;
iii) compute a POI projection line in the image frame corresponding to the POI projection location based on the calibration data; and
iv) determine the location of the POI in the tool frame based on at least the POI projection line and the mapping between the image frame and the tool frame.

12. The system of claim 11, wherein the processor is further configured to determine the location of the POI in the tool frame based additionally on selecting a location on the POI projection line based on intersecting the projection line with at least one line or surface in the tool frame on which the POI is known to lie.

13. The system of claim 12, wherein the at least one line or surface comprises a tooltip axis of rotation and the processor is further configured to select the location on the POI projection line by computing an intersection location between the POI projection line and the tooltip axis of rotation.

14. The system of claim 11, wherein determining the location of the POI in the tool frame comprises:
a second calibrated imaging device configured to capture a second image of the portion of the surface of the surgical tool from a different viewing angle than the first image, the second calibrated imaging device having second calibration data that enables the processor to map from a 2D location in the second image to a projection line in a second image frame, the second image frame being a 3D coordinate frame of the second calibrated imaging device,
wherein the processor is further configured to:
i) determine a mapping between the second image frame and the tool frame;
ii) recognize a second POI projection location on the second image based on the appearance of the portion of the surface of the tool in the second image;
iii) compute 2D coordinates for a second POI projection location on the second image;
iv) based on the second calibration data, compute a second POI projection line in the second image frame corresponding to the second POI projection location, and
v) determine the location of the POI in the tool frame by computing an intersection location between the POI projection line and the second POI projection line.

15. The system of claim 11, wherein the calibrated imaging device is further configured to capture a plurality of images of the portion of the surface of the surgical tool, each image in the plurality of images being taken from a different viewing angle, and
wherein the processor is further configured, for each image in the plurality of images, to:
i) recognize the POI projection location on that image based on the appearance of the portion of the surface of the tool in that image;
ii) compute 2D coordinates for the POI projection location on that image;
iii) based on the calibration data, compute a POI projection line in the image frame corresponding to the POI projection location on that image, and
iv) determine the location of the POI in the tool frame by computing an intersection location between each of the POI projection lines.

16. The system of claim 11, wherein the calibrated imaging device is configured to capture a plurality of images of the portion of the surface of the surgical tool, each image in the plurality of images having a different mapping between that image's frame and the tool frame, and
wherein the processor is further configured to:
i) compute a tool surface projection contour search region in each image in the plurality of images based on the mapping of each image, each tool surface projection contour search region having a plurality of pixel values;
ii) align the tool surface projection contour search regions in the plurality of images; and
iii) compute the POI projection location based on combining the pixel values in the aligned tool surface projection contour search regions such that pixel locations corresponding to aligned edges are distinguishable from pixel values corresponding to non-aligned edges.

17. The system of claim 11, wherein the processor is further configured to:
i) select a first location and a second location in the tool frame based on a spatial region defined by the surgical tool;
ii) map the first location and the second location from the tool frame to the image;

iii) resample the image in a rectangular grid to form a resampled image, the rectangular grid having rows and columns wherein the first location and the second location lie on the same row or column;
iv) use image processing to locate 2D coordinates for a resampled POI projection location in the image frame;
v) map the 2D coordinates of the resampled POI projection location to the image; and
vi) compute the 2D coordinates for the POI projection location on the image.

18. The system of claim 11, wherein the processor is further configured to:
store the location of the POI in a computer-readable memory, and
during a plurality of times in a time interval, at each time in the plurality of times in the time interval, the processor is configured to:
i) operate the surgical navigation system to determine a mapping between the image frame and the tool frame; and
ii) operate the processor to determine whether to update the stored POI location based on the mapping between the image frame and the tool frame.

19. The system of claim 11, wherein the surface of the surgical tool comprises a patient-contacting portion and the processor is further configured to obtain shape parameters of the patient-contacting portion.

20. The system of claim 11, wherein the processor is configured to determine the mapping between the image frame and the tool frame based on the image of the portion of the surface of the surgical tool.

* * * * *